(12) United States Patent
Sugiyama et al.

(10) Patent No.: US 9,039,880 B2
(45) Date of Patent: May 26, 2015

(54) DEVICE AND METHOD FOR MANUFACTURING THE SAME

(75) Inventors: Koji Sugiyama, Kyoto (JP); Rina Matsumi, Kyoto (JP); Satoshi Yonehara, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 519 days.

(21) Appl. No.: 13/242,761

(22) Filed: Sep. 23, 2011

(65) Prior Publication Data

US 2012/0138461 A1 Jun. 7, 2012

(30) Foreign Application Priority Data

Dec. 1, 2010 (JP) ................................. 2010-268366

(51) Int. Cl.
*G01N 27/447* (2006.01)
*B01L 3/00* (2006.01)
*B32B 3/02* (2006.01)
*B32B 3/26* (2006.01)
*B32B 3/30* (2006.01)
*B32B 7/10* (2006.01)
(Continued)

(52) U.S. Cl.
CPC .... *G01N 27/44791* (2013.01); *B01L 3/502707* (2013.01); *B01L 2300/0816* (2013.01); *B01L 2400/0421* (2013.01); *B29C 66/026* (2013.01); *B29C 66/028* (2013.01); *B29C 66/53461* (2013.01); *B29C 66/54* (2013.01); *B29L 2031/756* (2013.01); *B32B 3/02* (2013.01); *B32B 3/266* (2013.01); *B32B 3/30* (2013.01); *B32B 7/10* (2013.01); *B32B 7/12* (2013.01); *B32B 27/08* (2013.01); *B32B 27/16* (2013.01); *B32B 27/308* (2013.01); *B32B 37/0076* (2013.01); *B32B 37/203* (2013.01); *B32B 38/00* (2013.01); *B32B 38/0004* (2013.01); *B32B 2037/0092* (2013.01); *B32B 2038/0076* (2013.01); *B32B 2250/02* (2013.01); *B32B 2250/24* (2013.01); *B32B 2333/12* (2013.01); *C09J 5/02* (2013.01)

(58) Field of Classification Search
None
See application file for complete search history.

(56) References Cited

U.S. PATENT DOCUMENTS

| | | | |
|---|---|---|---|
| 6,176,962 B1 | 1/2001 | Soane et al. | |
| 6,568,910 B1 * | 5/2003 | Parce | 417/40 |

(Continued)

FOREIGN PATENT DOCUMENTS

| | | |
|---|---|---|
| CN | 101283042 A | 10/2008 |
| EP | 2144056 A1 | 1/2010 |

(Continued)

OTHER PUBLICATIONS

Wong et al., Microfluid Nanofluid, 2009,291-306.*

(Continued)

*Primary Examiner* — J. Christopher Ball
(74) *Attorney, Agent, or Firm* — Morgan, Lewis & Bockius LLP

(57) ABSTRACT

The present invention provides a device that decreases deformation during manufacturing of the device, provides a firm joint without use of an adhesive, and allows chemical modification of a channel during manufacturing of the device. The device includes two joined substrates, and a concavity is formed on at least one of the opposing surfaces of the two substrates so as to make a channel, where the two substrates are joined together by a covalent bond via a crosslinking agent (A), and the crosslinking agent (A) is exposed on an inner wall surface of the channel.

16 Claims, 10 Drawing Sheets

(51) Int. Cl.
*B32B 7/12* (2006.01)
*B32B 27/08* (2006.01)
*B32B 27/16* (2006.01)
*B32B 38/00* (2006.01)
*C09J 5/02* (2006.01)
*B29C 65/00* (2006.01)
*B29L 31/00* (2006.01)
*B32B 27/30* (2006.01)
*B32B 37/00* (2006.01)
*B32B 37/20* (2006.01)

(56) References Cited

U.S. PATENT DOCUMENTS

| | | | |
|---|---|---|---|
| 6,838,156 B1 | 1/2005 | Neyer et al. | 428/172 |
| 2002/0014306 A1 | 2/2002 | Virtanen | |
| 2002/0117517 A1 | 8/2002 | Unger et al. | |
| 2004/0228770 A1* | 11/2004 | Gandhi et al. | 422/102 |
| 2005/0230767 A1* | 10/2005 | Park et al. | 257/414 |
| 2006/0102478 A1 | 5/2006 | Robert et al. | 204/451 |
| 2009/0054264 A1 | 2/2009 | Ugolin et al. | 506/13 |
| 2009/0200166 A1 | 8/2009 | Nakayama et al. | 204/451 |
| 2009/0281250 A1* | 11/2009 | DeSimone et al. | 525/418 |
| 2010/0258211 A1 | 10/2010 | Burns et al. | |
| 2010/0282607 A1 | 11/2010 | Oishi et al. | 204/450 |

FOREIGN PATENT DOCUMENTS

| | | | |
|---|---|---|---|
| JP | 2000-297157 | 10/2000 | C08J 5/12 |
| JP | 2005-121443 | 5/2005 | G01N 33/53 |
| JP | 2005-140681 | 6/2005 | G01N 35/08 |
| JP | 2005-255615 | 9/2005 | C07F 7/18 |
| JP | 2006-145537 | 6/2006 | G01N 17/447 |
| JP | 2006-187730 | 7/2006 | B01J 19/00 |
| JP | 2007-237484 | 9/2007 | B29C 65/48 |
| JP | 4129054 | 5/2008 | G01N 27/26 |
| WO | WO 91/12904 | 9/1991 | B07D 57/02 |
| WO | WO 01/08802 | 2/2001 | B01L 7/00 |
| WO | 2007/021762 A2 | 2/2007 | |
| WO | WO 2008/029685 | 3/2008 | G01N 27/447 |
| WO | WO 2008/055080 | 5/2008 | G01N 33/543 |

OTHER PUBLICATIONS

Duffy et al., "Rapid prototyping of microfluidic switches in poly(dimethyl siloxane) and their actuation by electro-osmotic flow," J Micromech Microeng 9: 211-217 (1999).

Extended European Search Report issued in corresponding European Patent Application No. 11182934.7 mailed Mar. 23, 2012.

Office Action issued in corresponding Chinese Patent Application No. 201110297760.X dated Aug. 4, 2014.

* cited by examiner

DEVICE AND METHOD FOR MANUFACTURING THE SAME

BACKGROUND

1. Field

The present invention relates to a device and a method for manufacturing the same.

2. Description of Related Art

Recently, microchip devices (micro fluid devices) have been used as analytic tools in the fields of chemistry, biochemistry, pharmacology, medical science, and veterinary medicine such as genetic analyses, clinical diagnoses, drug screening and the like, and also for the syntheses of compounds. Use of microchip devices has advantages for example, the required quantity of a reagent can be reduced, and the time for analysis can be shortened in comparison with a conventional analysis. The analyses include an analysis of AFP as a protein in serum, prothrombin or the like. As another example, WO 2008/029685 proposes a method for separation analysis of hemoglobin A1c (HbA1c) by capillary electrophoresis performed with a microchip. Japanese Patent No. 4129054 discloses a method for measuring hemoglobin A1c to obtain a highly precise measurement of stable hemoglobin A1c by using electrophoresis, including fixing an ionic polymer on an inner face of an electrophoretic path, and using a buffer solution containing a sulfonated polysaccharide.

Conventionally, such microchip devices have been manufactured principally by using glass substrates. However, glass substrates cause problems. For example, they are easily broken due to impact, and the weight results in inconvenience in transportation or disposal. In order to cope with these problems, application of resin substrates is increased since resin is light-weight, nonbreakable and inexpensive. Techniques for joining resin products having micro channels include the use of adhesives and adhesion at a temperature not lower than the melting point of the resin. However, such techniques may result in problems such as deformation or blockade of the channels, which is caused by the adhesive or the molten resin entering the micro channels. For solving these problems, various joint techniques have been developed.

JP 2005-121443 A describes a process for oxidation-treating a surface of a plastic, a process for reduction-treating an oxygen-containing functional group generated by the oxidation-treatment, and a plastic substrate. JP 2006-187730 A describes a method for manufacturing a resin-made micro flow passage chemical device by pre-treating by irradiating surfaces to be joined of substrates with ultraviolet rays in vacuum; laminating these substrates thus irradiated on each other; and joining the laminated substrates to each other by heating them to a temperature lower than the plastic deformation temperature of the resin or pressurizing them without heating them. JP 2007-237484 A describes a method including: preparing ultraviolet permeable polymer materials as a solid and a liquid respectively, bringing the materials to get contact together, and heat-treating the materials so as to be joined mutually.

SUMMARY OF THE INVENTION

In manufacturing a microchip device, peeling of substrates on the interface will cause leakage of a sample from the channel. Since the channel is fine, even a trace of leakage will affect the fluid flow characteristics such as a flow velocity and a fluid pressure in the channel. Therefore, a sufficient joint strength is required. Similarly, other factors such as deformation and profile irregularity of the channel may affect the fluid flow characteristics.

In general, chemical modification on the inner face of the channel of the microchip device is carried out after formation of the channel, and thus the procedures become complicated. Chemical modification on the inner face of the channel is sometimes preferred for the purpose of generating an electroosmotic flow (EOF) inside the capillary channel or sometimes for suppressing generation such an electroosmotic flow. In an alternative case, chemical modification on the inner face of the channel is sometimes preferred in view of suppressing adherence or adsorption of the sample onto the inner face of the channel.

Therefore, with the foregoing in mind, the present invention provides a device that decreases deformation during manufacturing of the device, providing a firm joint between the substrates without use of an adhesive, and that allows chemical modification of a channel during manufacturing of the device. The present invention provides a method for manufacturing the device.

Viewed from one aspect, the present invention relates to a device including two joined substrates, where a concavity is formed on at least one of opposing surfaces of the two substrates so as to make a channel. The two substrates are joined together by a covalent bond via a crosslinking agent (A), and the crosslinking agent (A) is exposed on an inner wall surface of the channel.

Viewed from another aspect, the present invention relates also to a method for manufacturing a device that includes two joined substrates where a concavity is formed on at least one of opposing surfaces of the two substrates so as to make a channel. The method includes bringing a crosslinking agent (A) into contact with the opposing surfaces of the two substrates, superimposing the two substrates, and causing a reaction between the substrates, so that the two substrates join together by a covalent bond via the crosslinking agent (A) and that the crosslinking agent (A) is exposed on an inner wall surface of the channel.

According to the present invention, since the substrates are joined together by a covalent bond via a crosslinking agent (A), the substrates are joined firmly without use of an adhesive, and thus a device where deformation in the channel is suppressed can be provided. Furthermore, according to the present invention, a device where the crosslinking agent (A) used for the joint is exposed on the inner face of the channel can be provided. Further, according to the present invention, a method for manufacturing a device enabling chemical modification of the interior of the channel during manufacturing of the device can be provided.

BRIEF DESCRIPTION OF THE DRAWINGS

FIG. 2 includes schematic views showing a configuration of a device according to an embodiment of the present invention.

FIG. 5 includes schematic views showing a configuration of a device according to a second embodiment of the present invention.

FIG. 6 includes schematic views showing a configuration of a device according to a third embodiment of the present invention.

FIG. 7 includes schematic views showing a configuration of a device according to a fourth embodiment of the present invention.

FIG. 8 includes schematic views showing a configuration of a device according to a fifth embodiment of the present invention.

DETAILED DESCRIPTION OF THE INVENTION

Figure 1A:
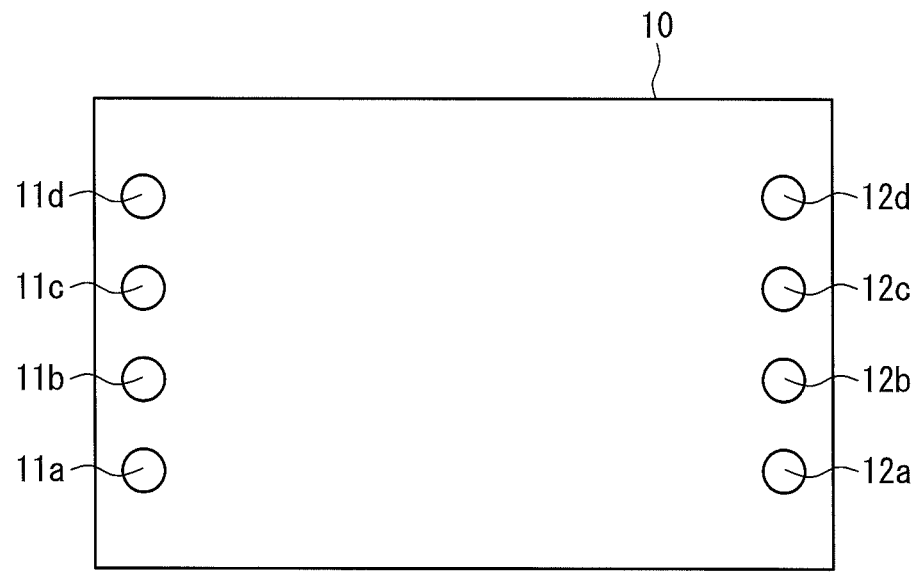
FIG. 1 is a schematic plan view showing a substrate of a device according to an embodiment of the present invention.

The present invention is based on a finding that, in a method for manufacturing a device with a channel provided by laminating two substrates, a crosslinking agent is used for both joining the substrates during manufacturing of the device and modification of the channel, thereby enabling a firm joint of the substrates, suppression of deformation of the channel and modification of the channel.

Namely, viewed from one aspect, the present invention relates to a device that includes two joined substrates where a concavity is formed on at least one of the opposing surfaces of the two substrates so as to make a channel. The two substrates are joined together by a covalent bond via a crosslinking agent (A), and the crosslinking agent (A) is exposed on the inner wall surface of the channel (hereinafter, this is also called "device of the present invention.").

In the device of the present invention, since the substrates are joined together by a covalent bond via the crosslinking agent (A), a firm joint between the substrates can be provided. In addition, since the joint can be carried out under a mild pressure and at a mild temperature in comparison with the conditions for a conventional pressure joint or a melt-joint, deformation of the channel can be decreased. Further, since the crosslinking agent (A) is exposed on the inner face of the channel, chemical modification of the inner face of the channel with the crosslinking agent (A) can be carried out simultaneously during manufacturing of the device (in particular, at the time of joining the substrates). Therefore, for example, in a case where the channel is a capillary, generation of the electroosmotic flow can be controlled simultaneously at the time of manufacturing the device (in particular at the time of joining the substrates).

[Substrate]

For the materials of the substrates used in the device of the present invention, inorganic materials and organic materials can be used. Though there is no particular limitation therefor, the examples include a resin substrate, a quartz substrate, a glass substrate and the like. Among them, from the viewpoint of easiness in handling and cost reduction, a resin substrate is preferred. For the material of the resin substrate, a material that is suitable for easy formation of a channel and difficult to deform is preferred, and a nonlimiting example thereof is a thermoplastic resin. Preferred examples of the thermoplastic resin include, but are not limited to, acrylic resins such as polymethyl methacrylate, polycarbonate, polyvinylidene chloride, cyclic polyolefin, polyether ether ketone, polystyrene and the like, from the viewpoint of easy formation of the channel and difficulty in deformation. Polymethyl methacrylate represents an exemplary embodiment. In some cases, materials of the two substrates used in the device of the present invention may be different from each other. The examples may include a combination of an inorganic material and an organic material, a combination of separate organic materials, and the like. Though the combination of an inorganic material and an organic material is not limited particularly, the examples include a combination of a quartz substrate and a thermoplastic resin, and the like. Though the combination of separate organic materials is not limited particularly, the examples include a combination of an acrylic resin and a cyclic polyolefin, and the like.

Regarding two substrates used in the device of the present invention, a concavity is formed on at least one of the opposing surfaces. This concavity is covered with the opposing surface of the other substrate, thereby a channel is formed. It is preferable that the dimension of the concavity corresponds to the below-mentioned channel. The concavity on the substrate surface can be formed by molding, etching, cutting or the like without any particular limitations. An open hole may be formed on the substrate as required. It is preferable that a below-mentioned functional group (D), a functional group (C), a crosslinking agent (B) and/or the crosslinking agent (A) have been introduced onto the opposing surface of the substrate. The thickness and/or the size of the substrates can be adjusted and/or selected appropriately.

[Channel]

The device of the present invention has a channel formed by joining substrates having concavities. The dimension, the length, and the shape of the channel are not limited particularly. One embodiment of the channel is a capillary. An example of the capillary is a channel having a cross section of circumcircle whose diameter is not more than 140 μm for example, generally in a range of 20 to 70 μm. The cross-sectional shape of the channel may be, for example, rectangular, semicircular, trapezoidal, circular, or elliptic. Further, the shape of the channel is not limited to linear, but it can be decided arbitrarily, for example to have a branch at the end part. The examples include a cross, a T-shape, a Y-shape, an X-shape and the like, and the shape may be a combination of these examples.

Regarding the channel in the device of the present invention, the crosslinking agent (A) is exposed on the inner wall surface. Therefore, in a case where the channel is a capillary and the crosslinking agent (A) is ionic, an electroosmotic flow can be generated by arranging an aqueous solution and by applying a voltage in the channel. On the other hand, if the crosslinking agent (A) is neutral, generation of the electroosmotic flow in the channel and the influence can be suppressed.

In the present specification, "the crosslinking agent (A) is exposed (on the surface of a substrate or the like)" indicates that the crosslinking agent (A) is fixed on the surface of the substrate in a state where one or at least two of the functional groups of the crosslinking agent (A) forms a covalent bond with another molecule, preferably with a molecule on the substrate. In the present specification, the crosslinking agent (A), the crosslinking agent (B), the functional group (C) and the functional group (D) each may indicate an agent or a group before reaction with the other molecule(s), and, without any particular notice, it may indicate also an agent or a group after reaction with the other molecule(s) and a reactive functional group that has been deactivated.

[Device]

The device of the present invention having a channel can be utilized as an apparatus, a tool or a chip for analyzing a sample. The device of the present invention can be utilized as a device, a tool, or a chip for performing operations such as mixing, extraction and phase separation or chemical reaction, and producing substances as required.

In an embodiment, the device of the present invention can be used for separation analysis of a sample. More specifically, the device can be made as a microchip for a capillary electrophoresis. The sample is not limited particularly, and it may be prepared from a sample material or it may be provided without any substantial pretreatment. The sample material is not limited particularly, and the examples include a sample of an aqueous solution, a biological sample, foods and the like. The biological sample is not limited particularly, and the examples include blood, a substance that is derived from blood and that contains components in blood, a culture solution of fungus or the like, an extract of a plant or the like, and so on. Examples of components in blood include serum, plasma, erythrocyte, leukocyte, thrombocyte and the like. An example of blood is blood collected from a living body. An example of the substance that is derived from blood and that contains erythrocyte components may be obtained by separating or preparing from blood and contains erythrocyte components. The examples include hemocyte fractions from which plasma has been eliminated, concentrated hemocyte, freeze-dried blood/hemocyte, a hemolysis sample prepared by subjecting whole blood to a hemolysis process, centrifuged blood, blood that has been subjected to spontaneous sedimentation, washed blood and the like. The analytical object is not limited particularly, and the examples include: a nucleotide chain (e.g., oligonucleotide chain, polynucleotide chain); chromosome; a peptide chain (e.g., C-peptide, angiotensin I, and the like); a protein (e.g., hemoglobin, hemoglobin A1c, immunoglobulin A, immunoglobulin E, immunoglobulin G, immunoglobulin M, albumin, decomposition products thereof, and the like); an enzyme (e.g., amylase, alkaline phosphatase, γ-glutamyl transferase, lipase, creatine kinase, lactate dehydrogenase, glutamate oxaloacetate transaminase, glutamate pyruvate transaminase); bacteria (e.g., *Mycobacterium tuberculosis, Streptococcus pneumoniae, staphylococcus, Escherichia coli, Helicobacter pylori*, and the like); viruses (e.g., herpesvirus, influenza virus, adenovirus, enterovirus, HBV, HCV, HIV and the like); fungus (e.g., *Candida, Cryptococcus* and the like); protein or peptide or carbohydrate antigen derived from microorganism; various allergens that cause allergy (e.g., house dust; mite; pollens of Japanese cedar, cypress, bitterweed and the like; and allergens derived from animals such as lobster/shrimp and crab, foods such as egg white, fungus, insects, medicine, chemical substances, and the like); lipid (e.g., lipoprotein and the like); tumor marker protein antigen (e.g., PSA, PGA and the like); sugar chain antigen (e.g., AFP, hCG, transferrin, IgG, thyroglobulin, CA19-9, prostate gland specific antigen, tumor marker sugar chain antigen having a special sugar chain produced by cancer cells, and the like); sugar chains (e.g., hyaluronic acid, β-glucan, sugar chain possessed by for example the above-mentioned sugar chain antigen or the like); hormones (e.g., T3, T4, TSH, insulin, LH, and the like); and chemical substances (e.g., endocrine disruptors such as nonyl phenol, 4-octyl phenol, benzophenone, and the like).

[Crosslinking Agent (A)]

Figure 4:
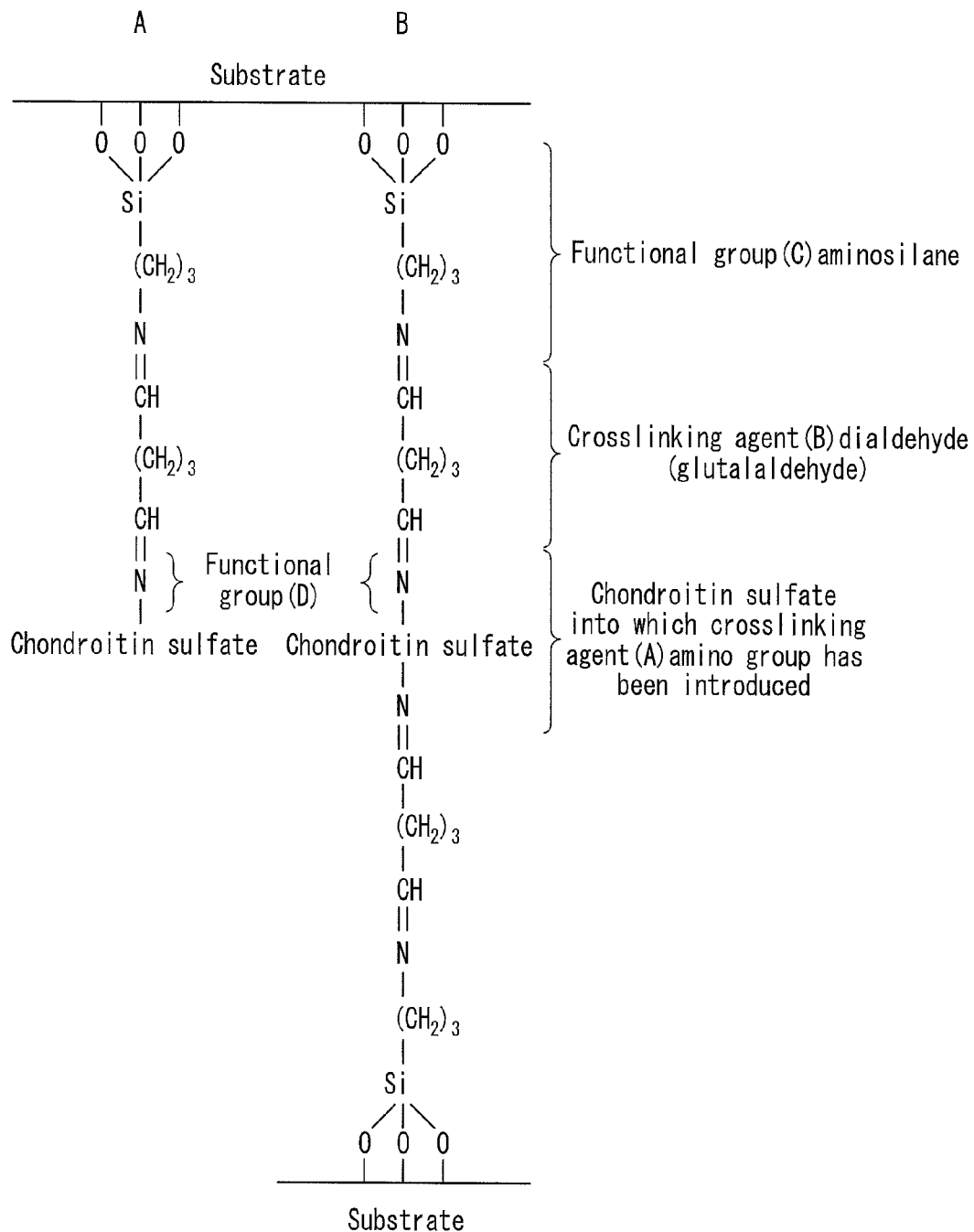
FIG. 4 includes schematic views for explaining an example of a modified state of a substrate surface (FIG. 4A) and an example of a joint state of the substrates (FIG. 4B).

In the present specification, the crosslinking agent (A) helps joint of the two substrates in the device of the present invention, and it is exposed on the inner wall surface of the channel in the device of the present invention. FIG. 4 shows an embodiment of the joint state of the substrates in the device of the present invention. In FIG. 4, the left-A is a schematic view showing a state where the crosslinking agent (A) is exposed on the inner wall surface of the channel; the right-B is a schematic view showing a state where the substrates are joined together via the crosslinking agent (A). The aminated chondroitin sulfate shown in FIG. 4 is a preferred example of the crosslinking agent (A). Another preferred example is aminated heparin or the like.

In an exemplary embodiment, it is preferable from the viewpoint of ease in manufacturing, that the crosslinking agent (A) is bonded to the functional group (C) on the substrate surface via the crosslinking agent (B). From the viewpoint of strengthening the joint between the substrates, it is preferable that the crosslinking agent (A) and the crosslinking agent (B) are covalently bonded to each other, and that crosslinking agent (B) and the functional group (C) are covalently bonded to each other. It is preferable that the crosslinking agent (A) has a plurality of functional groups (D) that can be covalently bonded to the crosslinking agent (B). Since the crosslinking agent (A) of one molecule is bonded to each of the crosslinking agent (B) of the separate substrates, a strong bond between the two substrates can be obtained.

In an exemplary embodiment, the crosslinking agent (A) may be a monomer that includes a double bond such as a vinyl group and that can be copolymerized with the crosslinking agent (B) that includes a double bond such as a vinyl group.

Furthermore, in another embodiment, the crosslinking agent (A) may be covalently bonded directly to the functional group (C) on the substrate surface. Namely, the bonding between the crosslinking agent (A) and the functional group (C) is obtained without the crosslinking agent (B). In this embodiment, it is preferable that the crosslinking agent (A) has a plurality of functional groups (D) that can be covalently bonded to the functional group (C). Alternatively, the crosslinking agent (A) may be a monomer that includes a double bond such as a vinyl group and that can be copolymerized with the functional group (C) that includes a double bond such as a vinyl group.

In the crosslinking agent (A), examples of the functional group (D) that will be bonded to the crosslinking agent (B), the functional group (C) and/or the crosslinking agent (A) itself include an amino group, a carboxyl group, a vinyl group and the like.

First Embodiment of Crosslinking Agent (A)

A first embodiment of the crosslinking agent (A) is an ionic group containing polysaccharide. Examples of the ionic group include a sulfate group, a carboxylic acid group, a phosphate group, an amino group and the like. Though there is no particular limitation, examples of the ionic group containing polysaccharide include a polysaccharide having a sulfate group, a polysaccharide having a carboxylic acid group, a polysaccharide having a phosphate group, a polysaccharide having an amino group, and the like. Examples of the polysaccharide having a sulfate group include glycosaminoglycan having a sulfate group, such as chondroitin sulfate, heparin, heparan sulfate, dermatan sulfate, keratan sulfate, carrageenan and the like. Examples of the polysaccharide having a carboxylic acid group include glycosaminoglycan having a carboxylic acid group, such as chondroitin sulfate, heparin, heparan sulfate, alginic acid, hyaluronic acid, pectic acid and the like. Examples of the polysaccharide having a phosphate group include phosphorylated polysaccharide produced by lactic acid bacteria or the like. Examples of the polysaccharide having an amino group include chitosan, chitin and the like. In a case where the glycosaminoglycan is N-acetylated, preferably the glycosaminoglycan is de-N-acetylated to be aminated. Examples of deacetylated glycosaminoglycan (aminated glycosaminoglycan) include aminated chondroitin sulfate, aminated heparin and the like. Chondroitin sulfate, keratan sulfate, hyaluronic acid, heparin, heparan sulfate and the like can be aminated by deacetylation with hydrazine. An alternative method for amination of the heparin and heparan sulfate is a method of using desulphation with pyrimidinium salt or the like. Examples of the functional group (D) in the crosslinking agent (A) of the first embodiment include a carboxyl group and an amino group.

[De-N-Acetylated Chondroitin Sulfate]

As mentioned above, de-N-acetylated chondroitin sulfate in the present specification denotes chondroitin sulfate (aminated chondroitin sulfate) prepared by eliminating the acetyl group at the N-acetyl group in chondroitin sulfate and by providing an amino group. Specifically, it denotes chondroitin sulfate subjected to a hydrazine process or the like. De-N-acetylated chondroitin sulfate suitable for the present invention has a de-N-acetylation rate of 5 to 100% for example, preferably 10 to 50%, and more preferably 10 to 25%.

Second Embodiment of Crosslinking Agent (A)

A second embodiment of the crosslinking agent (A) is a vinyl-based monomer. Though there is no particular limitation, the specific examples include acrylic monomers such as acrylic acid, vinyl sulfonic acid, 2-acrylamide-2-methyl propane sulfonic acid, methylenesuccinic acid, allylsulfonate, acrylamide, methacrylic acid, tertiary butyl acrylamide sulfonic acid and the like. The second embodiment includes an example where the crosslinking agent (A) copolymerizes with either the crosslinking agent (B) or the functional group (C).

Third Embodiment of Crosslinking Agent (A)

A third embodiment of crosslinking agent (A) includes an amino-group containing polymer. Though there is no particular limitation, the specific examples include polyethyleneimine, polyacrylamide, a copolymer of poly(acrylamide,N,N'-bisacrylamide), a copolymer of acrylamide and acrylic acid, a copolymer of acrylamide and vinyl sulfonic acid, and the like. Examples of the functional group (D) of the crosslinking agent (A) in the third embodiment include an amino group, a methoxy group and a carboxyl group.

[Crosslinking Agent (B)]

in the present specification, the crosslinking agent (B) intermediates the bonding between the crosslinking agent (A) and the functional group (C) on the substrate surface in one embodiment f a device according to the present invention, and it is covalently bonded to the crosslinking agent (A) and the functional group (C) respectively (FIG. 4).

First Embodiment of Crosslinking Agent (B)

A first embodiment of the crosslinking agent (B) corresponds to the first embodiment of the crosslinking agent (A), and the examples include dialdehydes having aldehyde groups at the both terminals, dicarboxylic acids having carboxylic acid groups at the both terminals, and diamines having amino groups at the both terminals. Specific examples for the first embodiment of the crosslinking agent (B) include glutaraldehyde, phthalaldehyde, isophthalaldehyde, terephthalaldehyde, 5-formyl salicylaldehyde, naphthalenedialdehyde, glutaric acid, spermine, spermidine, putrescine and the like.

Second Embodiment of Crosslinking Agent (B)

A second embodiment of the crosslinking agent (B) corresponds to the second embodiment of the crosslinking agent (A), and the examples include an amino group containing vinyl-based monomer. Specific examples of the amino group containing vinyl-based monomer include acrylamide monomers such as acrylamide, dimethylaminopropylacryl amide, and the like.

[Functional Group (C)]

In the present specification, the functional group (C) denotes a functional group to be introduced onto a substrate surface in one embodiment of a device according to the present invention, and it is to be covalently bonded to the crosslinking agent (B) (FIG. 4). Further, as described above, the functional group (C) may be a functional group to be covalently bonded directly to the crosslinking agent (A) in an alternative embodiment.

For the functional group (C), an amino group, a vinyl group, a carboxyl group, a methoxy group, an aldehyde group, and a hydroxyl group can be used preferably. In a case where the functional group (C) is an amino group, a vinyl group or a carboxyl group, introduction onto the substrate surface can be carried out by using an aminosilane compound, a vinylsilane compound, a carboxysilane compound or the like in a usual manner.

Examples of the aminosilane compound suitably used for introduction of an amino group include, but are not limited to, 3-aminopropyltriethoxysilane, 3-aminopropyltrimethoxysilane, 2-aminoethyl-3-aminopropylmethyldimethoxysilane, 2-aminoethyl-3-aminopropyltrimethoxysilane, N-2-(aminoethyl)-3-aminopropyltriethoxysilane, N-2-(aminoethyl)-3-aminopropyltrimethoxysilane, tris(dimethylamino)chlorosilane, tris(dimethylamino)silane and the like.

Examples of the vinylsilane compound suitably used for introduction of a vinyl group include, but are not limited to, vinyl triethoxysilane, vinyl methoxysilane, vinyltris(2-methoxyethoxy)silane, vinyl(trifluoromethyl)dimethylsilane, and the like.

Examples of the carboxysilane compound suitably used for introduction of a carboxyl group include, but are not limited to, p-methyldiethoxysilylethyl benzoic acid trimethylsilyl, p-dimethylethoxysilylethyl benzoic acid trimethylsilyl and the like, as described in Japanese Patent 4336970.

For the functional group (C), the functional group of the substrate itself can be used. The methoxy group is included in polymethylmethacrylate or the like, and the carboxyl group is included in polyacrylic acid or the like.

The method of introducing the functional group (C) onto the substrate surface may be determined in accordance with the materials of the substrate. When the substrate is made of an acrylic resin such as polymethylmethacrylate, it is possible to introduce the functional group (C) onto the substrate surface by nucleophilic addition-elimination reaction of primary/secondary amine to the acyl group of the methacrylic acid. Examples of the primary/secondary amine compound suitable for introduction of an amino group include, but are not limited to, 1,2-diaminopropane, 1,3-diaminopropane, 1,3-diamino-2-propanol, diaminopyridine and the like. Examples of the primary/secondary amine compound suitable for introduction of a vinyl group include, but are not limited to, acrylamide and the like. Examples of the primary/secondary amine compound suitable for introduction of a carboxyl group include, but are not limited to, 4-amino-benzoic acid, 3-amino-benzoic acid, 3-amino-isobutylic acid and the like. Alternatively, a methacrylate group in polymethylmethacrylate or the like can be substituted to the carboxyl group by subjecting the substrate surface to a strong base treatment for example. Alternatively, it is possible to introduce the carboxyl group by treating the substrate surface with VUV (vacuum ultraviolet), plasma or the like so as to substitute the methyl group or the like of the acrylic resin to the carboxyl group.

[Covalent Bond]

In the present specification, there is no particular limitation on the covalent bond between the crosslinking agent (A) and either the crosslinking agent (B) or the functional group (C), and the covalent bond between the crosslinking agent (B) and the functional group (C). The examples include Schiff's base formation between an amino group and an aldehyde group, an amide bond between an amino group and a carboxyl group, copolymerization between double bonds, an ether bond between a hydroxyl group and an epoxy group, and the like.

Combinations of the crosslinking agent (A), the crosslinking agent (B), the functional group (C) and the functional group (D) in the device of the present invention are indicated in the Table 1 below, though the present invention is not limited to these examples. In Table 1 below, a bond (A-B) and a bond (B-C) denote respectively a bond between the crosslinking agent (A) and the crosslinking agent (B), and a bond between the crosslinking agent (B) and the functional group (C). When the column for the crosslinking agent (B) is blank, it indicates a combination not including the crosslinking agent (B).

TABLE 1

| CE* | CA* (A) | FG* (D) | Bond (A-B) Bond (A-C) | CA* (B) | Bond (B-C) | FG* (C) |
|---|---|---|---|---|---|---|
| 1 | 1st embodiment: anion group | Carboxyl group | Amide bond | Diamines | Amide bond | Carboxyl group |
| 2 | containing polysaccharide (e.g., glycosaminoglycan) | Carboxyl group | Amide bond | — | | Amino group |
| 3 | 1st embodiment: anion group | Amino group | Schiff's base formation | Dialdehydes | Schiff's base formation | Amino group |
| 4 | containing polysaccharide (e.g., | Amino group | Amide bond | Dicarboxylic acids | Amide bond | |
| 5 | de-N-acetylated glycosaminoglycan) | Amino group | Amide bond | — | — | Carboxyl group |
| 6 | | Amino group | Aminomethyl | — | — | Methoxy group |
| 7 | 2nd embodiment: vinyl-based monomer | (Vinyl group) | Alkyl formation | Amino group containing vinyl-based monomer | Aminomethyl | Methoxy group |
| 8 | | (Vinyl group) | Alkyl formation | — | — | Vinyl group |
| 9 | 3rd embodiment: Amino group | Amino group | Aminomethyl | — | — | Methoxy group |
| 10 | containing polymer | Amino group | Amide bond | — | — | Carboxyl group |

CE: Combination example

CA: Crosslinking agent

FG: Functional group

EMBODIMENTS

Figure 1B:
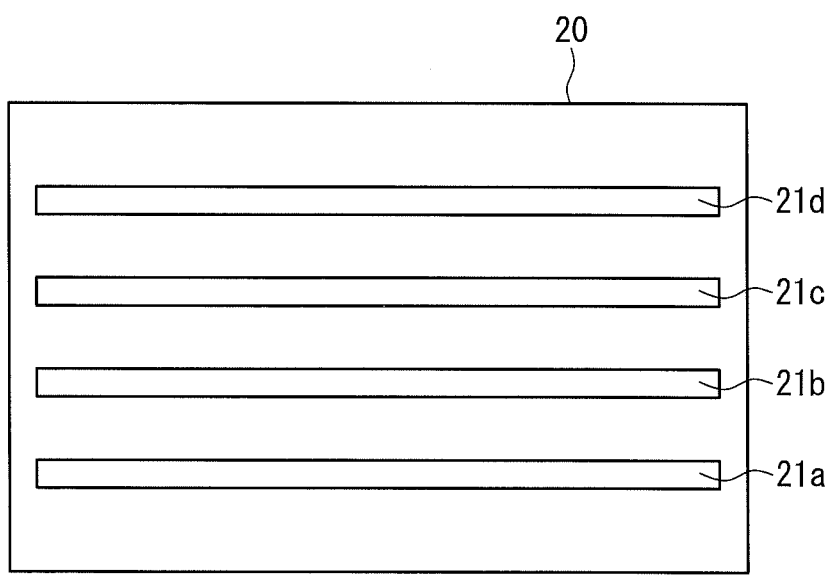
Figure 2A:
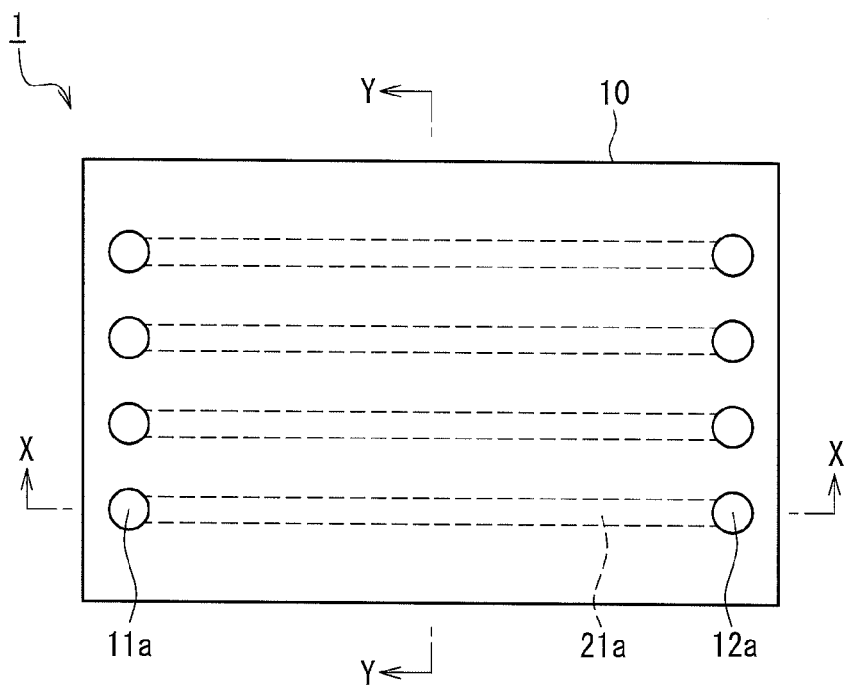
FIG. 2A is a plan view.
Figure 2B:
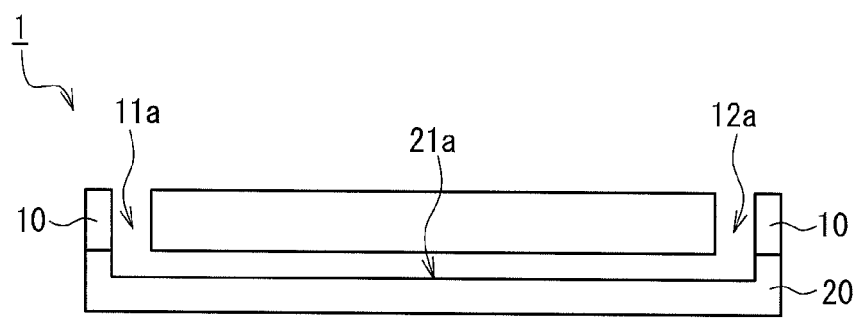
FIG. 2B is a cross-sectional view taken along a line X-X in FIG. 2A.
Figure 2C:
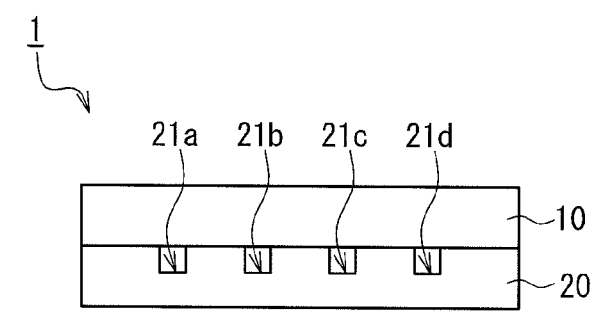
FIG. 2C is a cross-sectional view taken along a line Y-Y in FIG. 2A.

Hereinafter, a first embodiment of a device according to the present invention will be described by way of illustrative embodiments with reference to the drawings, although the present invention is not limited to the embodiment. FIG. 1 includes schematic plan views showing a substrate according to the first embodiment of a device of the present invention. FIG. 1A is a plan view showing a cover-side resin substrate 10, and FIG. 1B is a plan view showing a base-side resin substrate 20. FIG. 2 includes schematic views showing a configuration of the device in this embodiment of the present invention. FIG. 2A is a plan view, FIG. 2B is a cross-sectional view taken along a line X-X in FIG. 2A, and FIG. 2C is a cross sectional view taken along a line Y-Y in FIG. 2A.

A device 1 has two substrates (the resin substrate 10 and the resin substrate 20). The resin substrate 10 is set as a cover-side substrate, and the resin substrate 20 is set as a base-side substrate. The device 1 is shaped rectangular for example, and it is manufactured by joining the resin substrate 10 and the resin substrate 20 together. Each side of the device 1 has a length of 10 mm to 200 mm, for example.

For the resin substrates 10 and 20, a thermoplastic resin is used. For the thermoplastic resin, for example, an acrylic resin such as polymethylmethacrylate is used preferably. Alternatively, the thermoplastic resin may be polycarbonate, polyvinylidene chloride, cyclic polyolefin or the like, though the resin is not limited to these examples.

On the resin substrates 10 and 20, predetermined concavities such as grooves and holes have been formed. The resin substrates can be shaped predeterminedly by extrusion, injection, pressing, and machining. Two or more of these methods can be used, or the resin substrate 10 and the resin substrate 20 may be shaped by methods different from each other. From the viewpoint of formation of the resin substrates, the thickness of the resin substrates 10 and 20 is in a range of 0.2 to 5 mm for example.

On the base-side resin substrate 20, grooves 21a, 21b, 21c, and 21d (hereinafter, collectively called 'grooves 21') for making channels are formed. On the cover-side resin substrate 10, holes 11a, 11b, 11c and 11d (hereinafter, collectively called 'holes 11') and 12a, 12b, 12c and 12d (hereinafter, collectively called 'holes 12') penetrating in the thickness direction are formed. The holes 11 and 12 are formed so that they are positioned at the both ends of the grooves 21 when the resin substrate 10 and the resin substrate 20 are superimposed.

When the resin substrate 10 and the resin substrate 20 are superimposed and joined together, the openings of the grooves 21 on the resin substrate 20 are covered with the resin substrate 10 so that the grooves functions as channels. For an analysis, tubes, nozzles or the like have been fit in the holes 11 and 12 of the resin substrate 10 so as to allow communications, thereby introducing/discharging samples or the like into/from the channels through the holes 11 and 12.

The grooves 21 are designed to decrease the use amounts of the sample and the reagent, considering the formation precision or the like, so that the cross section of a channel will be a rectangle whose side has a length of 10 to 200 μm. The cross-section of the channel may be semicircular, trapezoidal, circular, or elliptic. For example, in the cross sectional view of device 1 in FIG. 2C, the channel is designed to be a square of 40 μm×40 μm, and thus each groove 21 is shaped to be 40 μm in width and in depth. The sizes of the holes 11 and 12 may be determined in accordance with the analyzing apparatus or the analysis method. For example, the holes may be circles having a diameter of about 2 mm.

FIGS. 5-8 show other embodiments of the device of the present invention. In FIGS. 5-8, components identical or similar to those in the above-mentioned embodiment are assigned with identical reference numbers.

Figure 5A:
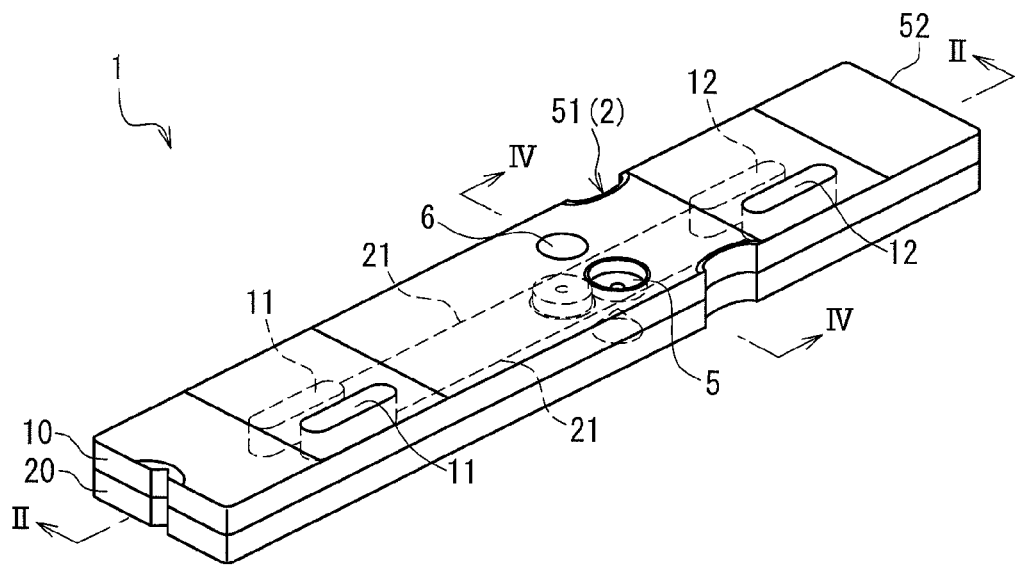
FIG. 5A is a schematic perspective view.
Figure 5B:
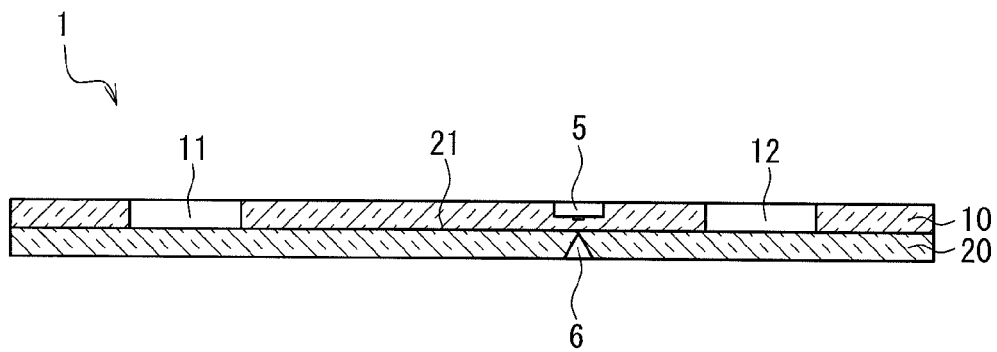
FIG. 5B is a cross-sectional view taken along a line II-II in FIG. 5A.
Figure 5C:
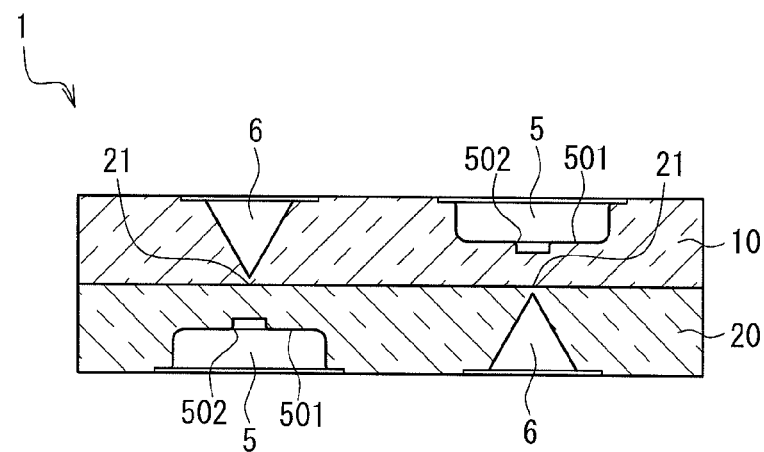
FIG. 5C is a cross-sectional view taken along a line IV-IV in FIG. 5A.

FIG. 5 shows a second embodiment of the device of the present invention. FIG. 5A is a schematic perspective view showing the device of the second embodiment. FIG. 5B is a cross-sectional view taken along a line II-II in FIG. 5A. FIG. 5C is a cross-sectional view taken along a line IV-IV in FIG. 5A. The device 1 in the second embodiment is manufactured by superimposing and joining the cover-side resin substrate 10 and the base-side resin substrate 20 together, and the device 1 has a positioning region 2, grooves (channels) 21, holes 11 and 12, a light emission cavity 5, and a light reception cavity 6. Since the device in the second embodiment of the present invention has the positioning region 2, it is possible to determine the positions of the resin substrates 10 and 20 accurately and laminate them during manufacturing of the device, and to mount accurately in an analyzing apparatus during use of the device. The size of the device 1, the material and thickness of the resin substrates 10 and 20, and the shape and size of the grooves 21 can be substantially same as the examples mentioned above.

The positioning region 2 is used to determine the positions of the resin substrates 10, 20 or the device 1 in manufacture or use of the device 1. For example, it includes a positioning dent 51 and a positioning plane 52. By using the positioning dent 51 and the positioning plane 52, a further accurate positioning can be carried out. The positioning dent 51 can be formed as a longitudinal dent on a longer side of the resin substrates 10 and 20. The positioning dent 51 may be formed, for example, on the both longer sides of the resin substrates 10 and 20 as shown in FIG. 5A. The positioning plane 52 may be formed as a plane perpendicular to the longitudinal direction of the resin substrates 10 and 20.

In the device 1 in the second embodiment, a channel 21 that enables analyses using capillary electrophoresis is formed on each of the cover-side resin substrate 10 (the upper face in FIG. 5) and the base-side resin substrate 20 (the lower face in FIG. 5). Namely, the device 1 in the second embodiment has two channels 21. In each of the channels 21, holes 11 and 12, a light emission cavity 5, and a light reception cavity 6 are formed.

The light emission cavity 5 is a site at which a light beam for an analysis using the capillary electrophoresis will enter, and it is formed to be located above each of the channels 21 on the resin substrates 10 and 20. The light emission cavity 5 is shaped to be concave in the thickness direction from the surfaces of the resin substrate 10, 20. The light emission cavity 5 may be formed of an outer concavity 501 and an inner concavity that is formed inward in the outer concavity 501 in the thickness direction of the resin substrate 10 and 20. The sizes of the outer concavity 501 and the inner concavity 502 can be determined suitably in accordance with the sizes or the like of the resin substrates 10 and 20 and the channels 21, without any particular limitations. For example, the outer concavity 501 may have a depth of about 0.8 mm and a circular cross section about 3 mm in diameter. The inner concavity 502 may have a depth of about 0.2 mm and a circular cross section about 0.6 mm in diameter.

The light reception cavity 6 is a site from which a light beam for an analysis using the capillary electrophoresis will be emitted, and it is formed in each of the resin substrates 10 and 20 for the purpose of enabling reception of a light beam from the light emission cavity 5. The light reception cavity 6 is shaped to be concave in the thickness direction from each of the surfaces of the resin substrates 10 and 20. The shape of the light reception cavity 6 is not limited particularly, and it can be substantially conical. The size of the light reception cavity 6 can be determined suitably in accordance with the sizes of the resin substrates 10 and 20, the channels 21 and the light emission cavity 5 or the like, without any particular limitations. For example, the opening can be a circle having a diameter of about 2 mm, and the depth may be about 0.13 mm.

The holes 11 and 12 are used to introduce/discharge samples into/from the channels 21, and they are formed respectively at the both ends of each channels 21. A means for applying voltage necessary for the capillary electrophoresis can be inserted into the holes 11 and 12. The cross-sectional shapes of the holes 11 and 12 are not limited particularly, and for example, they can be elliptic, circular, and the like. Though the sizes of the holes 11 and 12 are not limited particularly, the holes may be 5.6 mm in the longitudinal direction and 1.2 mm in the transverse direction, for example.

Figure 6A:
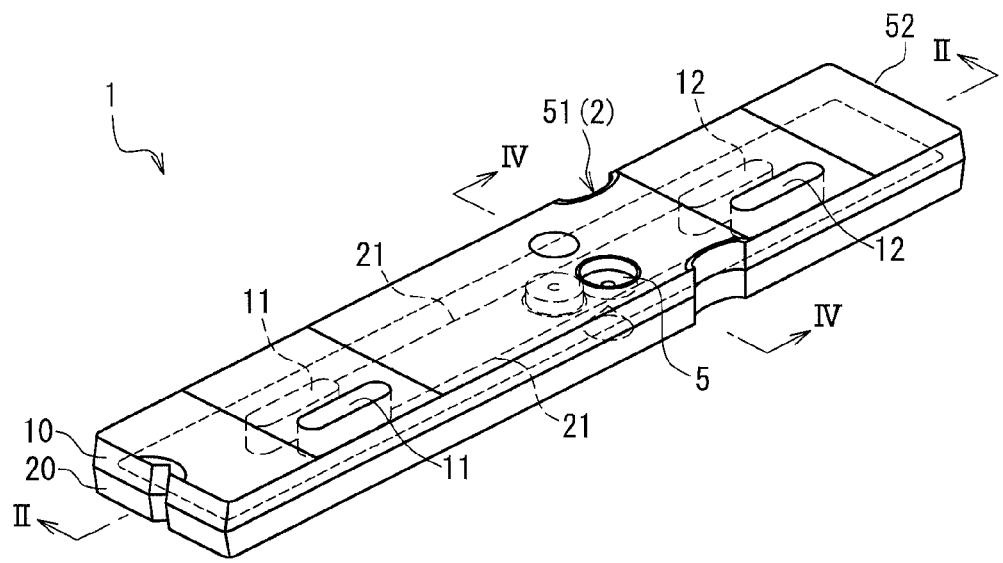
FIG. 6A is a schematic perspective view.
Figure 6B:
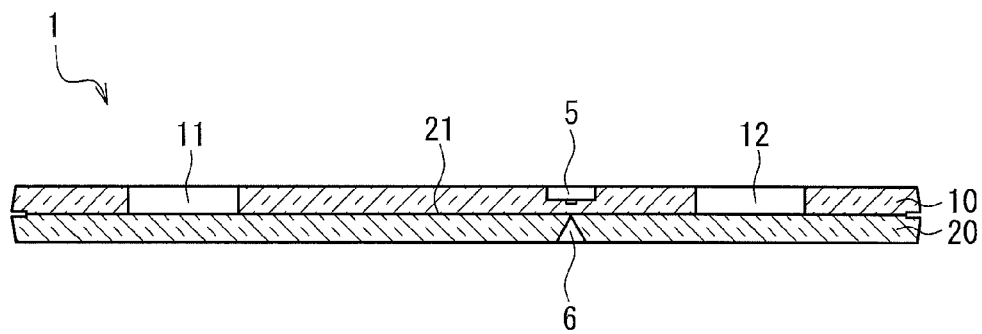
FIG. 6B is a cross-sectional view taken along a line II-II in FIG. 6A.
Figure 6C:
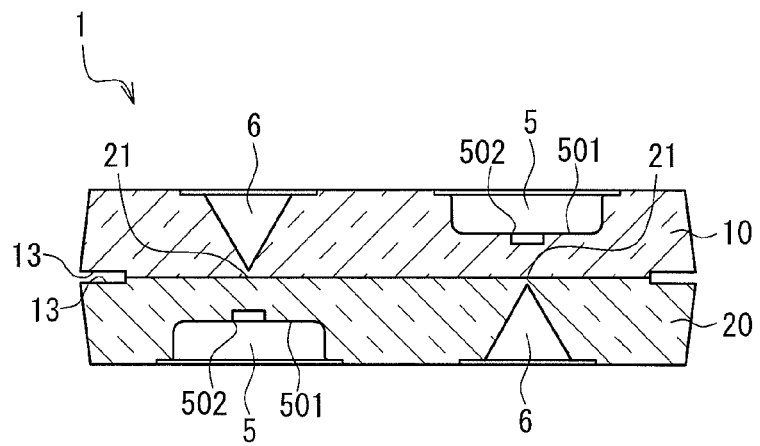
FIG. 6C is a cross-sectional view taken along a line IV-IV in FIG. 6A.

FIG. 6 shows a third embodiment of the device of the present invention. FIG. 6A is a schematic perspective view showing the device of the third embodiment. FIG. 6B is a cross-sectional view taken along a line II-II in FIG. 6A. FIG. 6C is a cross-sectional view taken along a line IV-IV in FIG. 6A. The device 1 in the third embodiment is as same as the device in the second embodiment except that a transverse groove 13 is formed on the side face of the device 1, namely, in the vicinity of the interface between the resin substrate 10 and the resin substrate 20. The transverse groove 13 is formed around the side face of the device 1. Since the device according to the third embodiment has the positioning region 2 and the transverse groove 13, it is possible to determine more accurately the positions of the resin substrate 10 and 20 in manufacturing the device, and it is possible to mount to the analyzing apparatus more accurately in use of the device.

As shown in FIG. 6C, the transverse groove 13 is formed to concave from the end faces (side faces) of the resin substrates 10 and 20 inward (along the interface of the resin substrates 10 and 20). Specifically, the transverse groove 13 is composed of an inner side face including a border on the interface between the resin substrate 10 and the resin substrate 20, and a bottom face formed from the inner side face toward the end faces (side faces) of the resin substrates 10 and 20. Though the size of the transverse groove 13 is not limited particularly, for example, the transverse groove 13 is about 0.1 mm in the thickness direction and about 1.0 min in the width direction. In the present invention, the shape of the transverse groove 13 is not limited to the shape as shown in FIG. 6B, but it may be for example a V-shape, a U-shape and the like.

Figure 7A:
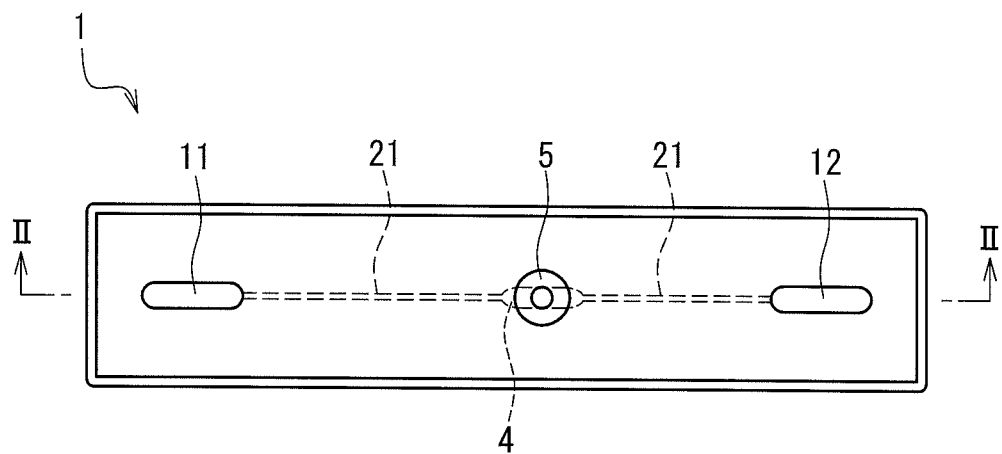
FIG. 7A is a top view.
Figure 7B:
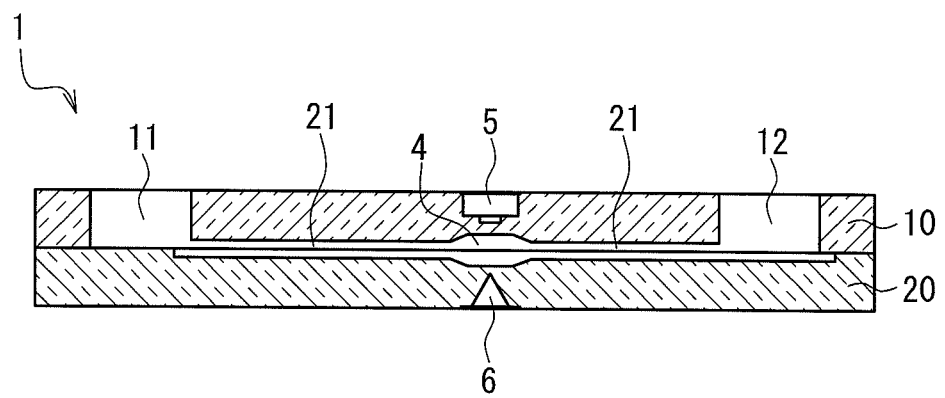
FIG. 7B is a cross-sectional view taken along a line II-II in FIG. 7A.

FIG. 7 shows a fourth embodiment of the device of the present invention. FIG. 7A is a top view showing the device of the fourth embodiment. FIG. 7B is a cross-sectional view taken along a line II-II in FIG. 7A. A device 1 according to the fourth embodiment is configured by superimposing and joining a cover-side resin substrate 10 and a base-side resin substrate 20 together. The device 1 includes a channel 21, a light emission cavity 5, a light reception cavity 6 and holes 11 and 12. And a light-transmitting section 4 is formed in the channel 21. The light emission cavity 5, the holes 11 and 12 are formed in the resin substrate 10, and the light reception cavity 6 is formed in the resin substrate 20.

The light-transmitting section 4 is a site to transmit a light beam for measuring absorbance. The light emission cavity 5 is formed in the resin substrate 10 positioned above the light-transmitting section 4 (upper face side in FIG. 7B), and the light reception cavity 6 is formed in the resin substrate 20 positioned below the light-transmitting section 4 (lower face side in FIG. 7B). When an analytical object passes the light-transmitting section 4, the light that travels from a light-emitting section (not shown) to a light-receiving section (not shown) through the light-transmitting section 4 is absorbed partly by a specific substance. At this time, a change in the light amount is detected. This is a so-called absorbance measurement. With reference to this principle, the concentration (throughput) of the specific substance (for example, HbA1c etc.) is detected.

The shape and size of the light-transmitting section 4 are not limited particularly. For example, as shown in FIGS. 7A and 7B, at the light-transmitting section 4, a plane (cross section) perpendicular to the longitudinal direction of the channel 21 is larger both in the lengthwise direction and the crosswise direction than the channel 21. According to this embodiment, since the path of the light passing the light-transmitting section 4 becomes long, the detection precision can be improved further. Furthermore, since the cross section is larger in both the lengthwise direction and the crosswise direction than the channel 21, it is possible to suppress disturbance in the flow from the channel 21 to the light-transmitting section 4.

It is preferable that tapered regions are formed between the light-transmitting section 4 and the channel 21. One of the tapered regions has a cross section increasing its size gradually from the channel 21 toward the light-transmitting section 4, and the other tapered region has a cross section decreasing its size gradually from the light-transmitting section 4 toward the channel 21. Though the inclination angle of the tapered regions is not limited particularly, it can be set to 30° for example. Though the cross sectional shape of the light-transmitting section 4 is not limited particularly, the examples include a circle, an ellipse, a rectangle and the like. In a case where the channel 21, the light-transmitting section 4 and the tapered regions are rectangular, from the viewpoint of suppressing turbulence in the flow from the channel 21 to the light-transmitting section 4, it is preferable that the cross-sectional aspect ratio is 0.8 to 1.2, more preferably 1.0 (square). In a case where the cross sections of the channel 21, the light-transmitting section 4 and the tapered regions are circular or elliptic, from the viewpoint as mentioned above, it is preferable that the cross-sectional aspect ratio is 0.8 to 1.2.

Figure 8A:
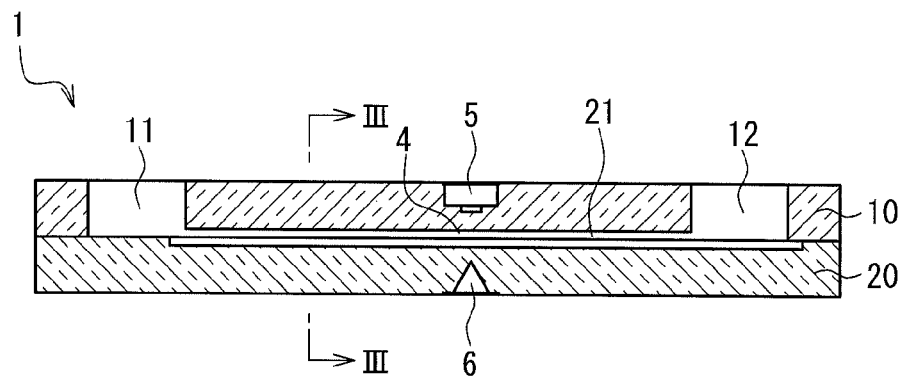
FIG. 8A is a cross-sectional view.
Figure 8B:
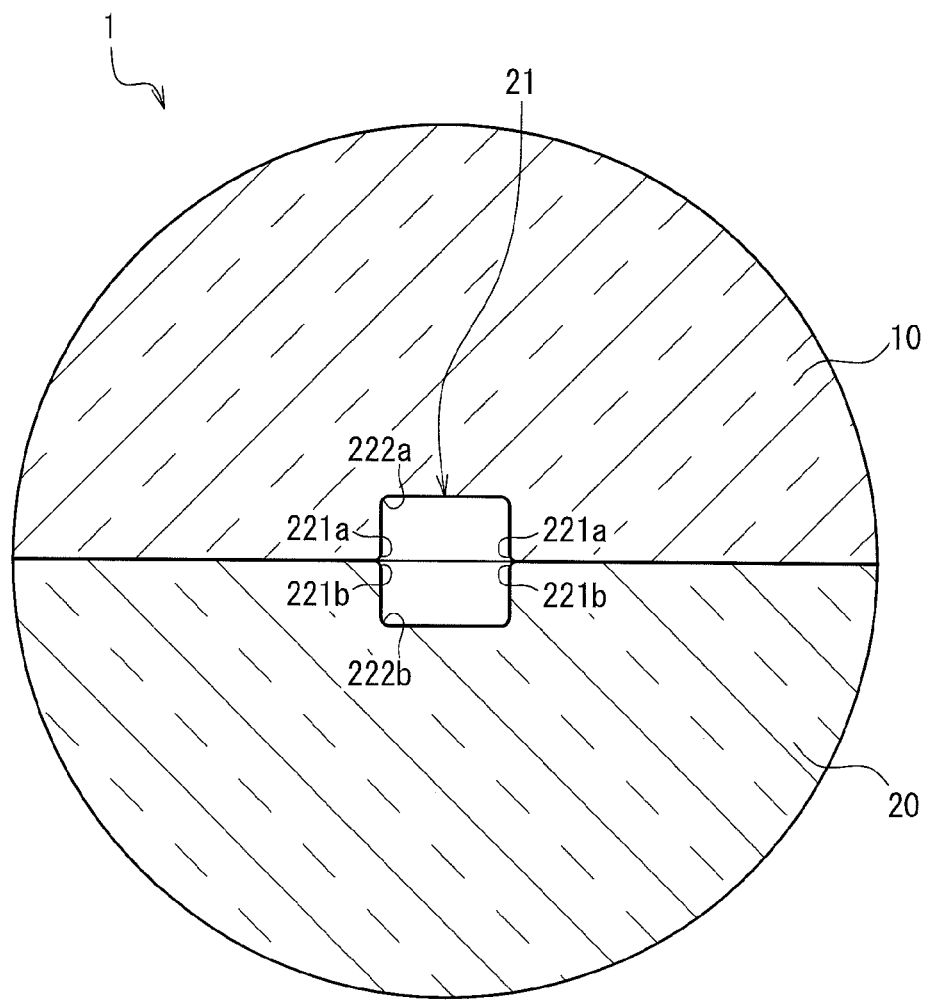
FIG. 8B is a cross-sectional view taken along a line III-III in FIG. 8A.

FIG. 8 shows a fifth embodiment of the present invention. FIG. 8A is a cross-sectional view showing a device according to the fifth embodiment, and FIG. 8B is a cross-sectional view taken along a line III-III in FIG. 8A. The device 1 in the fifth embodiment is configured by superimposing and joining a cover-side resin substrate 10 and a base-side resin substrate 20 together, and it includes a channel 21, a light emission cavity 5, a light reception cavity 6, and holes 11 and 12. The light emission cavity 5 and the holes 11, 12 are formed in the resin substrate 10, and the light reception cavity 6 is formed in the resin substrate 20. The channel 21 makes a light-transmitting section 4 in a region between the light emission cavity 5 and the light reception cavity 6.

From the viewpoint of preventing a sample such as blood from accumulating on the wall surface of the channel 21, it is preferable that the resin substrates 10 and 20 have curved edges 221a, 221b at the interface between the resin substrates 10 and 20. It is more preferable that the edges 221a and 221b are curved as a whole. For the purpose of preventing further effectively the sample such as blood from accumulating and for the purpose of improving the analytical precision, the radius of the curve is 5 μm or less, and preferably 2 μm. The radius of the curve can be determined suitably in accordance with the size of the channel 21. Preferably for example, it is not more than 10% of the lengthwise and crosswise lengths of the cross section of the channel 21.

From the viewpoint of preventing a sample such as blood from accumulating and for the purpose of improving the analytical precision, the corners 222a, 222b of the wall face forming the channel 21 are curves. It is preferable that the radius of the curve is larger than the radius of the edges 221a, 221b for example.

From the viewpoint of preventing a sample such as blood from accumulating on the wall surfaces of the holes 11 and 12, it is preferable that the edge of the resin substrate 10 is curved at the interface between the resin substrate 10 and the resin substrate 20, and more preferably, the edge is curved as a whole. The radius of the curve is substantially the same as that of the channel 21.

Though FIGS. 8A and 8B show an example where grooves are formed on both the resin substrate 10 and 20 thereby forming a channel 21, the present invention is not limited to this example. In an alternative example, grooves are formed on the resin substrate 20 alone, and the channel 21 is made by laminating the resin substrate 20 with the grooves and the resin substrate 10 without a groove. In this case, the edge of the resin substrate 20 can be curved in the region to be contact with the resin substrate 10. The shape of the channel 21 is not limited particularly, and the examples include a circle, a rectangle, a U-shape, a V-shape and the like.

[Method for Manufacturing Device]

In another aspect, the present invention relates to a method for manufacturing a device including two joined substrates, where a concavity is formed on at least one of the opposing surfaces of the two substrates, thereby making a channel. A crosslinking agent (A) is brought into contact with the opposing surfaces of the two substrates, the two substrates are superimposed and a reaction is caused between the superimposed substrates, so that the two substrates are joined together by a covalent bond via the crosslinking agent (A) and at the same time, the crosslinking agent (A) is exposed on the inner wall surface of the channel (hereinafter, they may be called "manufacturing method of the present invention").

The device of the present invention can be manufactured according to the manufacturing method of the present invention. According to the manufacturing method of the present invention, since the substrates are joined together by a covalent bond via the crosslinking agent (A), the substrates can be joined firmly together without use of an adhesive, and a device where deformation of channels are suppressed can be provided. Further, according to the manufacturing method of the present invention, a device where the crosslinking agent (A) used for the joint is exposed on the inner face of the channel can be provided. Furthermore, according to the manufacturing method of the present invention, the interior of the channel can be chemically modified during manufacturing of the device.

In the manufacturing method of the present invention, the details for the substrates, the channels, the device, the crosslinking agents (A) and (B), and the functional groups (C) and (D) are described above and indicated in the Table 1.

As Embodiment 1 of the manufacturing method of the present invention, a manufacturing method including the following steps will be described. The embodiment 1 may correspond to the combination examples 1, 3, 4 and 7 in the above Table 1, or preferably the combination examples 1, 3 and 4.

(1-a) The functional group (C) is introduced onto the substrate surface.

(1-b) The crosslinking agent (B) is brought into contact and reaction with the functional group (C) on the substrate surface.

(1-c) The crosslinking agent (A) is applied on one of the substrates to be superimposed, and subsequently, the other substrate is superimposed to cause a reaction between the crosslinking agent (A) and the crosslinking agent (B), and the substrates are joined together and at the same time, the interior of the thus formed channel is modified with the crosslinking agent (A).

Hereinafter, a method for manufacturing a device, which includes the steps (1-a) to (1-c), will be described with reference to FIG. 3. FIG. 3 includes diagrams showing an example of a method for manufacturing a device in the embodiment 1.

Regarding the step (1-a), an embodiment to introduce the functional group (C) as an amino group onto the substrate by use of an aminosilane compound is described. A person skilled in the art would carry out easily the method of introducing an amino group onto the substrate by using an aminosilane compound, with reference to a conventional technique. For example, in a case where an OH group is present on the substrate surface, the functional group (C) (amino group) can be introduced onto the substrate surface by only contacting the aminosilane compound. The condition for the reaction at this time is for example, the temperature is 10 to 120° C. and the time period is 10 to 60 minutes.

Figure 3A:
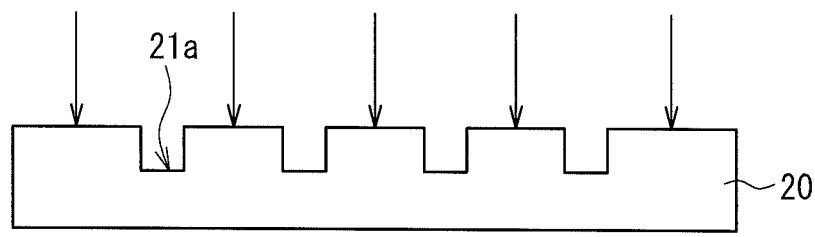
FIG. 3 includes diagrams showing an example of a method for manufacturing a device according to an embodiment of the present invention.
Figure 3B:
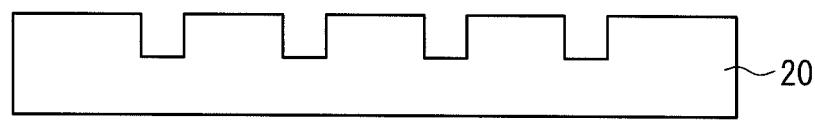

On the other hand, in a case where the substrates are made of an acrylic resin or the like having a low reactivity with regard to the aminosilane compound, it is possible to introduce an amino group for example, with reference to JP 2005-121443. Namely, the substrate surface is activated by oxidizing the substrate by use of vacuum ultraviolet rays, plasma treatment, corona discharge, flaming, ozonation or the like (FIG. 3A), thereby allowing the aminosilane compound to react to form silanol (FIG. 3B).

The following description refers to an embodiment for the above step (1-b), where a dialdehyde (glutaraldehyde) having aldehyde groups at the both terminals (crosslinking agent (B)) is brought into contact and reaction with the amino group (functional group (C)) on the substrate surface. A person skilled in the art would perform this reaction appropriately. For example, it is possible to dip a substrate onto which an amino group has been introduced in an aqueous solution of glutaraldehyde (0.1 to 10 wt %) at temperature of 10 to 40° C., which subsequently can be shaken or set aside for 30 minutes to 2 hours for causing the reaction.

Figure 3C:
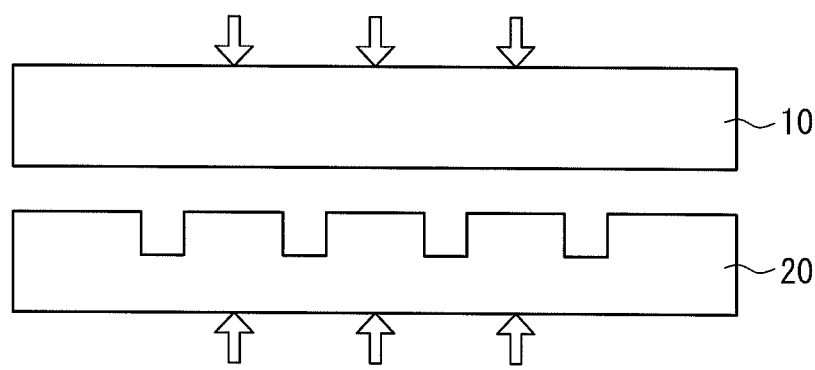
Figure 3D:
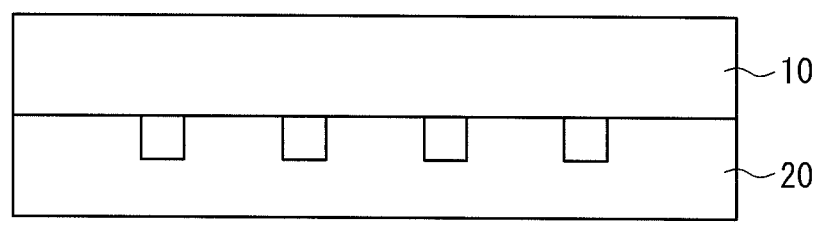

The following description refers to an embodiment for the above step (1-c), where the substrates onto which the glutaraldehyde (crosslinking agent (B)) has been introduced are joined with an anion group containing polysaccharide having an amino group (crosslinking agent (A)). Specifically, an anion group containing polysaccharide having an amino group (0.1 to 8 wt % aqueous solution) is applied on at least one of the substrates 10 and 20 onto which an aldehyde group has been introduced, and the substrates are brought into close contact together (FIGS. 3C and 3D). The substrates are applied with pressure of 1 to 1,000,000 Pa (0.000001 to 10 Kg/cm$^3$), such as 1 to 100,000 Pa (0.000001 to 1 Kg/cm$^3$) while being applied with heat of 20 to 60° C. for 30 seconds to 60 minutes, thereby a device of the present invention can be obtained.

Controlling the reaction of deacetylation and/or desulphation helps also to control the amount of the amino group of the anion group containing polysaccharide. When the amount of the amino group is increased, the sites to react with the aldehyde group derived from the glutaraldehyde is increased, thereby the joint strength can be enhanced.

Further, the aldehyde group derived from the glutaraldehyde residing at the parts not to be joined can be deactivated as required. Processes for deactivation include bringing the aldehyde group into contact with sodium hydrogen sulfite, amidosulfonic acid, sodium hydroxide and the like. Further, by setting the pH to be not lower than 11, the crosslinking reaction of the glutaraldehyde is accelerated and the aldehyde groups can be eliminated.

Embodiment 2 of the manufacturing method of the present invention includes the following steps. The embodiment 2 may correspond to the combination examples 1, 3, 4 and 7 in the above Table 1, preferably the combination examples 1, 3 and 4.

(2-a) The functional group (C) is introduced onto the substrate surface.
(2-b) The crosslinking agent (A) is brought into contact and reaction with the crosslinking agent (B).
(2-c) The crosslinking agent (A-B) bound substance obtained in the step
(2-b) is applied on the substrate surface onto which the functional group (C) has been introduced, and subsequently, the other substrate is superimposed to cause a reaction between the crosslinking agent (B) and the functional group (C), and the substrates are joined together and at the same time, the interior of the thus formed channel is modified with the crosslinking agent (A).

The step (2-a) is substantially the same as the step (1-a). The crosslinking agent (A-B) bound substance obtained in the above step (2-b) is, for example, a substance obtained by bonding chondroitin sulfate with a plurality of glutaraldehydes. In the step (2-c), this is arranged between the substrates onto which a functional group (C) has been introduced, thereby causing a reaction.

Embodiment 3 of the manufacturing method of the present invention includes the following steps. The embodiment 3 may correspond to the combination examples 1, 3, 4 and 7 in the above Table 1, preferably the combination examples 1, 3 and 4.

(3-a) The functional group (C) is introduced onto the substrate surface.
(3-b') The crosslinking agent (B) is brought into contact and reaction with the functional group (C) on the substrate surface.
(3-b") The crosslinking agent (A) and the crosslinking agent (B) are brought into contact and reaction with each other.
(3-c) The crosslinking agent (A-B) bound substance obtained in the step (3-b") is applied on the substrate surface onto which the crosslinking agent (B) has been introduced, and subsequently, the other substrate is superimposed so as to cause a reaction between the crosslinking agent (A) and the crosslinking agent (B) and also a reaction between the crosslinking agent (B) and the functional group (C), and the substrates are joined together and at the same time, the interior of the thus formed channel is modified with the crosslinking agent (A).

Embodiment 4 of the manufacturing method of the present invention includes the following steps. The embodiment 4 may correspond to the combination examples 2, 5, 6, 8-10 in the above Table 1.

(4-a) The functional group (C) is introduced onto the substrate surface.
(4-b) The crosslinking agent (A) is applied on the substrate surface onto which the functional group (C) has been introduced, and subsequently, the other substrate is superimposed to cause a reaction between the crosslinking agent (A) and the functional group (C), and the substrates are joined together and at the same time, the interior of the thus formed channel is modified with the crosslinking agent (A).

Embodiment 5 of the manufacturing method of the present invention includes the following steps. The embodiment 5 may correspond to the combination examples 1, 3, 4 and 7 in the above Table 1, preferably, the combination examples 7.

(5-a) The crosslinking agent (A) is brought into contact and reaction with the substrate surface having the functional group (C).
(5-b) The crosslinking agent (A) is applied on the substrate surface onto which the crosslinking agent (B) has been introduced, and subsequently, the other substrate is superimposed to cause a reaction between the crosslinking agent (A) and the crosslinking agent (B), and the substrates are joined together and at the same time, the interior of the thus formed channel is modified with the crosslinking agent (A).

For the specific example of the above step (5-a), acrylamide (crosslinking agent (B)) is brought into contact with the methoxy group (functional group (C)) on the surface of an acrylic resin substrate, thereby forming aminovinyl under an alkaline condition so as to bond the crosslinking agent (B) to the functional group (C). And, in the next step (5-b), vinyl sulfonic acid (crosslinking agent (A)) is applied, the substrates are superimposed and covalently bonded to join the substrates together, and at the same time, the interior of the thus formed channel is modified with vinyl sulfonic acid. In general, it is preferable that an initiator is used for the copolymerization reaction. Examples of the initiator include, but are not limited to: inorganic peroxides such as potassium persulfate, ammonium persulfate, and hydrogen peroxide; organic peroxides such as t-butyl peroxide, cumene hydroperoxide, and paramenthane peroxide; and azo-compounds such as azobis di-isobutyl nitryl, and 2,2'-azobis(2-amidinopropane)dihydrochloride. Persulfates such as potassium persulfate, ammonium persulfate and the like are preferred. For a polymerization promoter, it is possible also to use sodium hydrogensulfite, ammonium ferrous sulfate and the like.

Embodiment 6 of the manufacturing method of the present invention includes the following steps. The embodiment 6 may correspond to the combination examples 2, 5, 6, 8-10 in the above Table 1, preferably, the combination example 8.

(6-a) After applying the crosslinking agent (A) onto the substrate surface having the functional group (C), the other substrate is superimposed to cause a reaction between the crosslinking agent (A) and the functional group (C), and the substrates are joined together and at the same time, the interior of the thus formed channel is modified with the crosslinking agent (A).

As mentioned above, according to the manufacturing method of the present invention, the device of the present invention can be manufactured. Therefore, in a further aspect, the present invention relates to a device that is manufactured by the manufacturing method of the present invention. In the device manufactured by the manufacturing method of the present invention, since the substrates are joined firmly together and since the crosslinking agent (A) is exposed on the inner wall surface of the channel, generation of an electroosmotic flow can be controlled.

[Measuring Method]

In a further aspect, the present invention relates to a method for measuring a sample by using the device of the present invention. According to the measuring method of the present invention, since a device including substrates joined firmly together is used, stable measurement of samples can be carried out. Further, according to the measuring method of the present invention, since a device where generation of an electroosmotic flow is controlled is used, precision in measurement of an analytical object in a sample can be improved, and preferably, it is possible to improve the separation precision of the analytical object and/or to shorten the time for the measurement.

It is preferable that a measurement with a device includes a separation of an analytical object in a sample by a separation analysis. An example of the separation analysis is an electrophoresis, and in particular, a capillary electrophoresis is preferred. Though there is no particular limitation on the capillary electrophoresis, examples include electrokinetic chromatography, capillary zone electrophoresis, micellar electrokinetic chromatography, capillary gel electrophoresis, and the like. The sample and the analytical object in the measuring method of the present invention have been discussed above.

Regarding the measuring method of the present invention, the following explanation relates to a case where the capillary electrophoresis is used for the separation analysis. It should be noted however, that the following discussion is just an example, and the present invention is not limited thereto.

First, the channel (groove) of the device is filled with a running buffer. The filling with the running buffer can be carried out by utilizing a pressure, a capillary phenomenon or the like. Alternatively, a device having a channel filled in advance with the running buffer may be used. The running buffer can be determined appropriately in accordance with the types of the sample and the analytical object for example.

Next, the sample is introduced from one of the holes formed in the channel, and a voltage is applied between electrodes arranged at each of the holes positioned at the both ends of the channel. Thereby, the sample migrates from the hole through which the sample has been introduced to the other hole. The voltage to be applied to the both ends of the channel is not limited particularly, and it can be determined appropriately in accordance with the sample, then analytical object and the running buffer. The voltage is 0.5 to 10 kV for example, such as 0.5 to 5 kV.

In a case where a device where the crosslinking agent (A) exposed on the inner wall surface of the channel is ionic is used, an electroosmotic flow is generated in the channel due to application of voltage. In a case where the crosslinking agent (A) exposed on the inner wall surface of the channel is anion, the electroosmotic flow becomes a flow running from the positive pole to the negative pole. By generating such an electroosmotic flow, even if a positive pole is arranged at the hole through which the sample including a substance having a negative charge is introduced, the separation analysis can be performed by migrating the substance having a minus charge into the channel.

For the running buffer, a running buffer containing a cathodic polymer may be used. Thereby, the cathodic polymer in the running buffer bonds electrically to a substance having a positive charge in the sample. As a result, even if the difference of the positive charge between the substances contained in the sample is slight, the substances can be separated and analyzed. In this case, the electric charge of the substance formed by bonding the substance having a positive charge and the cathodic polymer becomes a negative charge. Therefore, it is preferable that an electroosmotic flow directed from the positive pole to the negative pole is generated in the channel. This embodiment can be applied preferably to a measurement where the analytical object is HbA1c, for example. In a case where the analytical object is HbA1c, there is no particular limitation for the cathodic polymer. For example, however, an anion group containing polysaccharide, an anion group containing acrylic polymer or the like is preferred. Further preferred examples include, but are not limited to, a carboxyl group containing polysaccharide, a sulfonated polysaccharide, a carboxyl group containing acrylic polymer, or a sulfonated acrylic polymer.

In a case where a device in which the crosslinking agent (A) exposed on the inner wall surface of the channel is not ionic is used, an separation analysis can be performed in a state where generation of the electroosmotic flow in the channel is suppressed. This embodiment can be applied preferably to a measurement for separating hemoglobin species (JP 2006-145537 A)

Then, the measurement is carried out at a predetermined site. The measurement can be carried out by an optical technique. Examples of the optical technique include, but are not limited to, absorbance measurement, transmittance measurement, reflectance measurement, fluorometry and the like. The measurement wavelength can be determined appropriately in accordance with the sample, the analytical object and the like.

The explanation in the above example refers to a method of measurement carried out by filling the channel of the device with a running buffer. The present invention is not limited to this example, and the separation analysis can be carried out by filling the channel of the device with a gel for example. The gel for filling is not limited particularly. Preferably, however, it has the same or similar nature as the crosslinking agent (A) exposed on the inner wall surface of the channel of the device. In a case of using a gel of polyacrylic acid, for example, a crosslinking agent based on polyacrylic acid may be used as the crosslinking agent (A) exposed on the inner wall surface of the channel of the device.

Figure 9:
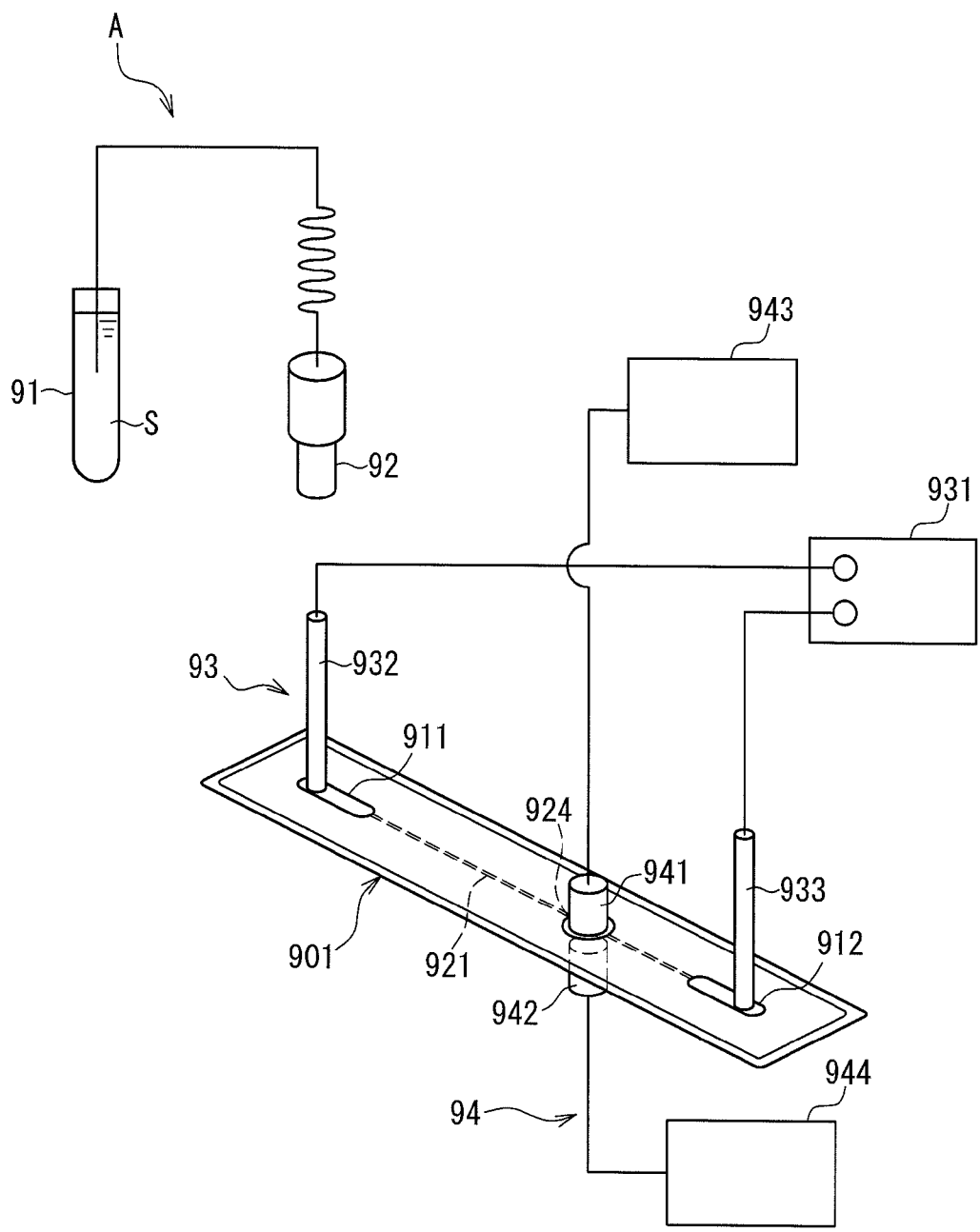
FIG. 9 is a schematic view showing an example of an analyzing apparatus that can be used for a measurement using the device of the present invention.

The measurement of the present invention can be carried out by use of the analyzing apparatus as shown in FIG. 9, for example. FIG. 9 is a schematic view showing an example of analyzing apparatus that can be used for measurement in the present invention. As shown in FIG. 9, the analyzing apparatus A has a sample container 91, a sample-introducing nozzle 92, a voltage applicator 93 and an analyzer 94, in which a device 901 can be mounted.

The sample container 91 and the sample-introducing nozzle 92 are used for introducing a sample into one of the holes (for example, a hole 911) of the device 901.

The voltage applicator 93 has a power source section 931, and electrodes 932, 933. The electrodes 932 and 933 are arranged respectively at holes 911 and 912 formed at the both ends of a channel 921 of the device 901. By applying a voltage between the electrodes 932, 933 by use of the power source section 931, a capillary electrophoresis can be performed within the channel 921.

The analyzer 94 is formed of a light-emitting section 941, a light-receiving section 942, a light source section 943 and a detecting section 944. The light source section 943 serves to generate light used for measurement, and it has a laser device, an LED or the like. In a case where the analytical object is hemoglobin for example, it is preferable that the light source section 943 generates light having a wavelength of 415 nm. The light-emitting section 941 is connected through for example optical fibers or the like, so that the light from the light-source section 943 is emitted from the light-emitting section 941 toward a detecting section 924. The light-receiving section 942 receives the light from the detecting section 924, and the received light is detected at the detecting section 944.

[Analyzing System]

In another aspect, the present invention relates to an analyzing system that includes the device of the present invention and a measuring apparatus that has a device-mounting section to which the device is mounted and that analyzes a sample by using the device. In the analyzing system of the present invention, since the device of the present invention where the substrates are joined firmly together is provided, a stable measurement of the sample can be carried out.

Measurement of an analytical object by use of the analyzing system of the present invention is substantially the same as the measuring method of the present invention. Further, the measuring apparatus in the analyzing system of the present invention is not limited particularly as long as the measuring apparatus has a device-mounting section to which the device is mounted and performs an analysis by use of a separation analysis. A known measuring apparatus can be used for this purpose, for example, the above-mentioned analyzing apparatus configured as shown in FIG. 9 can be used. In the analyzing system of the present invention, it is preferable that the device is detachable.

EXAMPLE 1

A device was manufactured by using the following substrates.

[Substrate]

A pair of microchip substrates made of PMMA (polymethylmethacrylate) as shown in FIGS. 1A and 1B were used.

[Introduction of Amino Group onto Substrate]

An amino group was introduced onto the substrate under the condition below.

1. The substrate made of PMMA was irradiated with vacuum ultraviolet rays.
2. The thus irradiated substrate, which was obtained in the above step 1, was dipped for 1 hour at 30° C. in an aqueous solution of 2% 3-amino propyl trimethoxy silane (Trade name: KBM903 supplied by Shin-Etsu Silicone).

[Bonding of Glutaraldehyde to Substrate]

Under the following condition, glutaraldehyde was introduced onto the substrate onto which an amino group had been introduced.

3. The substrate obtained in the above step 2 by introducing thereon an amino group was dipped in an aqueous solution of 1©% glutaraldehyde, and allowed to react for 2 hours in a 37° C. oven.

[Joint of Substrates and Modification of Channel with Chondroitin Sulfate]

4. Chondroitin sulfate into which an amino group had been introduced (de-N-acetylated chondroitin) was applied on the substrate onto which the aldehyde group derived from the glutaraldehyde group obtained in the above step 3 had been introduced, and the other substrate onto which the aldehyde group derived from the glutaraldehyde group obtained in the above step 3 was placed thereon, and the substrates were joined together by applying heat and pressure (60° C.; 20000 Pa).

[Deactivation of Glutaraldehyde Residing in Channel by Use of Amidosulphuric Acid]

5. Amidosulphuric acid was passed through the channel of the microchip obtained in the above step 4, thereby allowing a reaction at 37° C.

[Result]

The microchip obtained in the above step 5 was a favorable device where the substrates were joined firmly together and there was no substantial deformation of channel or leakage from the channel. Further, the electroosmotic flow measured in the following manner was 0.9 mm/sec. In the measurement, the anode was filled with an aqueous solution of 30 mM sodium chloride, and the cathode and the channel (capillary) were filled with an aqueous solution of 50 mM sodium chloride. A voltage of 120 V was applied, and the change in the current value was observed to measure the value of the electroosmotic flow.

EXAMPLE 2

Measurement of HbA1c was carried out by a separation analysis (capillary electrophoresis) by using a microchip formed as shown in FIG. 5.

[Microchip]

A microchip was prepared in a manner as recited in Example 1, where substrates made of PMMA were used for the substrates.

[Running Buffer]

A liquid containing 100 mmol/L malic acid and 10 g/L chondroitin sulfate C was adjusted by using arginine so as to have pH 5.0.

[Sample]

A running buffer was added to GHb trol 2x (supplied by Sysmex Corporation) and solved therein, thereby preparing a sample containing HbA1c.

[Measurement of EOF Velocity]

The EOF velocity was measured in the same manner as Example 1. The EOF velocity was 0.9 mm/sec.

[Measurement of HbA1c]

Figure 10:
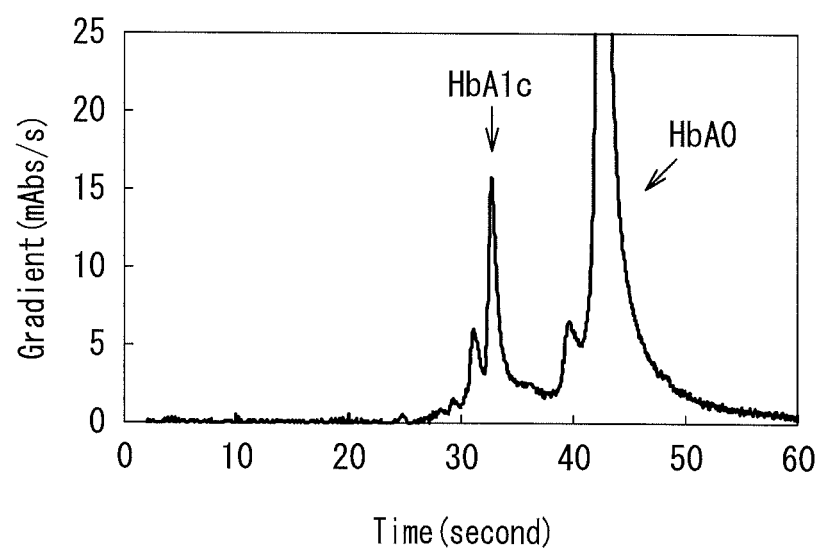
FIG. 10 is a graph showing an example of results in Example 2.

The running buffer was introduced into the hole 12 of the microchip, and the groove (capillary) 21 was filled with the running buffer by a capillary phenomenon. Next, the sample was introduced into the hole 11 of the microchip. For performing electrophoresis, a positive pole was set at the hole 11 of the microchip, while a negative pole was set at the hole 12 of the microchip, which were then charged with electricity at 1200 V for 60 seconds, thereby measurement was carried out. The HbA1c was measured by irradiating the light reception cavity 6 of the microchip with LED (wavelength 415 nm) from right below, and by disposing an optical detector right above the light emission cavity 5. The results are shown in FIG. 10.

[Result]

The thus obtained microchip was a favorable device having substrates that are joined firmly together and free of channel deformation and liquid leakage from the channel. Since the microchip has a fast EOF, the microchip of this example could separate HbA1c from the other Hb (hemoglobin) in a short time, and the separation precision was improved.

INDUSTRIAL APPLICABILITY

The present invention is useful in the fields of medicine, foods, and chemistry or the like where component analyses and separation analyses are performed.

The invention may be embodied in other forms without departing from the spirit or essential characteristics thereof. The embodiments disclosed in this application are to be considered in all respects as illustrative and not limiting. The scope of the invention is indicated by the appended claims rather than by the foregoing description, and all changes which come within the meaning and range of equivalency of the claims are intended to be embraced therein.

What is claimed is:

1. A device comprising two joined substrates, where a concavity is formed on at least one of opposing surfaces of the two substrates so as to make a channel,
    wherein the two substrates are joined together by a covalent bond via a crosslinking agent (A), and the crosslinking agent (A) is exposed on an inner wall surface of the channel, the crosslinking agent (A) consisting of an ionic group containing polysaccharide.

2. The device according to claim 1, wherein the channel is a capillary, an aqueous solution is arranged and a voltage is applied in the channel and an electroosmotic flow is generated.

3. The device according to claim 1, wherein the crosslinking agent (A) is bonded to a functional group (C) on the substrate surface via a crosslinking agent (B), the crosslinking agent (A) and the crosslinking agent (B) are covalently bonded to each other, and the crosslinking agent (B) and the functional group (C) are covalently bonded to each other.

4. The device according to claim 1, wherein the crosslinking agent (A) is bonded to a functional group (C) on the substrate surface, and the crosslinking agent (A) and the functional group (C) are covalently bonded to each other.

5. The device according to claim 1, wherein the covalent bond is selected from the group consisting of a Schiff's base formation between an amino group and an aldehyde group, an amide bond between an amino group and a carboxyl group, a copolymerization between double bonds, and an ether bond between a hydroxyl group and an epoxy group.

6. The device according to claim 3, wherein the crosslinking agent (B) is a dialdehyde having aldehyde groups at both terminals.

7. The device according to claim 3, wherein the functional group (C) is selected from the group consisting of an amino group, a carboxyl group, a methoxy group, a vinyl group, an aldehyde group, and a hydroxyl group.

8. A method for manufacturing a device that comprises two joined substrates, wherein a concavity is formed on at least one of opposing surfaces of the two substrates so as to make a channel, the method comprising:
   bringing a crosslinking agent (A) into contact with the opposing surfaces of the two substrates, superimposing the two substrates and causing a reaction between the superimposed two substrates, so that the two substrates join together by a covalent bond via the crosslinking agent (A) and that the crosslinking agent (A) is exposed on an inner wall surface of the channel, the crosslinking agent (A) consisting of an ionic group containing polysaccharide.

9. The method for manufacturing a device according to claim 8, further comprising:
   bringing a crosslinking agent (B) into contact and reaction with a functional group (C) present on the opposing surfaces of the two substrates so as to introduce the crosslinking agent (B) onto the two substrates by a covalent bond; and
   applying the crosslinking agent (A) on one of the two substrates onto which the crosslinking agent (B) has been introduced, superimposing the other of the two substrates so as to cause a reaction between the crosslinking agent (A) and the crosslinking agent (B), and joining the two substrates together by the covalent bond while modifying the interior of the thus formed channel with the crosslinking agent (A).

10. The method for manufacturing a device according to claim 8, further comprising:
    bringing the crosslinking agent (A) and a crosslinking agent (B) into contact and reaction so as to make a crosslinking agent bound substance (A-B); and
    applying the crosslinking agent bound substance (A-B) on one of the pair of substrates having the functional group (C) present on the surface, superimposing the other substrate so as to cause a reaction between the crosslinking agent (B) and the functional group (C), and joining the substrates together by the covalent bond while modifying the interior of the thus formed channel with the crosslinking agent (A).

11. The method for manufacturing a device according to claim 8, further comprising:
    applying the crosslinking agent (A) on one of the two substrates having a functional group (C) present on the surface, superimposing the other substrate so as to cause a reaction between the crosslinking agent (A) and the functional group (C), and joining the substrates together by the covalent bond while modifying the interior of the thus formed channel with the crosslinking agent (A).

12. The method for manufacturing a device according to claim 10, further comprising introducing the functional group (C) onto the opposing substrate surface.

13. The method for manufacturing a device according to claim 10, wherein the crosslinking agent (B) is a dialdehyde having aldehyde groups at both terminals.

14. The method for manufacturing a device according to claim 9, wherein the functional group (C) is selected from the group consisting of an amino group, a carboxyl group, a methoxy group, a vinyl group, an aldehyde group, and a hydroxyl group.

15. A method for measuring an analytical object present in a sample, comprising
    introducing the sample to the device according to claim 1,
    performing a separation analysis of the sample by capillary electrophoresis; and
    measuring the amount of the separated analytical object.

16. An analyzing system comprising the device according to claim 1 and a means for measuring an analytical object present in a sample, where the means for measuring comprises a means for mounting the device and for performing an analysis of the sample.

* * * * *